(12) United States Patent
Kawasaki

(10) Patent No.: US 9,642,535 B2
(45) Date of Patent: May 9, 2017

(54) MEDICAL IMAGE PROCESSING APPARATUS AND MEDICAL IMAGE PROCESSING METHOD

(71) Applicant: TOSHIBA MEDICAL SYSTEMS CORPORATION, Otawara-Shi (JP)

(72) Inventor: Tomohiro Kawasaki, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 95 days.

(21) Appl. No.: 14/830,827

(22) Filed: Aug. 20, 2015

(65) Prior Publication Data
US 2016/0058306 A1  Mar. 3, 2016

(30) Foreign Application Priority Data
Aug. 27, 2014  (JP) ................. 2014-172800

(51) Int. Cl.
*G06K 9/00* (2006.01)
*A61B 5/02* (2006.01)
(Continued)

(52) U.S. Cl.
CPC ........ *A61B 5/02014* (2013.01); *A61B 5/0042* (2013.01); *A61B 5/4064* (2013.01);
(Continued)

(58) Field of Classification Search
CPC ............................. A61B 5/02014; G06T 7/30
See application file for complete search history.

(56) References Cited

U.S. PATENT DOCUMENTS

2010/0185091 A1* 7/2010 Sumi ................. A61B 8/08
600/443
2011/0142322 A1* 6/2011 Kabus ................ G06T 3/0075
382/131
(Continued)

FOREIGN PATENT DOCUMENTS

JP 2011-4923 1/2011
JP 2011-104206 6/2011

OTHER PUBLICATIONS

M.D. Ford et al. "An objective approach to digital removal of saccular aneurysms: technique and applications", The British Journal of radiology, 82, 2009, 7 pages.

*Primary Examiner* — Oneal R Mistry
(74) *Attorney, Agent, or Firm* — Oblon, McClelland, Maier & Neustadt, L.L.P.

(57) ABSTRACT

A medical image processing apparatus includes a processing circuitry. The processing circuitry sets a first region and a second region different from the first region on first volume data and sets the first and second regions on second volume data, the first regions each including an observation target. The processing circuitry performs a former alignment on the second regions of the first and second volume data. The processing circuitry performs a latter alignment on the first regions of the first and second volume data by using a result of the former alignment. The processing circuitry applies a measurement condition used for a measurement of the observation target in the first volume data to a measurement of the observation target in the second volume data by using a result of the latter alignment.

16 Claims, 9 Drawing Sheets

(51) Int. Cl.
*A61B 5/00* (2006.01)
*G06T 7/00* (2017.01)
*G06T 7/30* (2017.01)
*A61B 90/00* (2016.01)

(52) U.S. Cl.
CPC .......... *A61B 5/7425* (2013.01); *G06T 7/0016* (2013.01); *G06T 7/30* (2017.01); *A61B 2090/374* (2016.02); *A61B 2090/378* (2016.02); *A61B 2090/3762* (2016.02); *G06T 2207/30016* (2013.01); *G06T 2207/30101* (2013.01)

(56) References Cited

U.S. PATENT DOCUMENTS

| | | | |
|---|---|---|---|
| 2013/0182008 A1* | 7/2013 | Zhou | G06T 11/60 345/629 |
| 2013/0301381 A1* | 11/2013 | Song | G06T 15/08 367/7 |
| 2014/0094680 A1* | 4/2014 | Kowarschik | A61B 6/507 600/407 |
| 2014/0219537 A1* | 8/2014 | Carelsen | G06T 7/0042 382/132 |

* cited by examiner

FIRST VOLUME DATA    SECOND VOLUME DATA

FIRST VOLUME DATA    SECOND VOLUME DATA

PORTION IN LARGE ROI
IN FIRST VOLUME DATA

MEDICAL IMAGE PROCESSING APPARATUS AND MEDICAL IMAGE PROCESSING METHOD

CROSS-REFERENCE TO RELATED APPLICATION

This application is based upon and claims the benefit of priority from Japanese Patent Application No. 2014-172800, filed on Aug. 27, 2014, the entire contents of which are incorporated herein by reference.

Further, the contents of Japanese Patent Application No. 2015-159423, filed on Aug. 12, 2015, which claims priority to Japanese Patent Application No. 2014-172800 are also incorporated herein by reference in their entirety.

FIELD

An embodiment as an aspect of the present invention relates to a medical image processing apparatus and a medical image processing method for aligning data including information on blood vessels.

BACKGROUND

A cerebral aneurysm refers to an aneurysm as a result of swelling of a part of a blood vessel and develops without symptoms until it ruptures and presents as a subarachnoid hemorrhage in many cases. A target of surgical treatments had been a ruptured cerebral aneurysm until recently which caused subarachnoid hemorrhage or a giant cerebral aneurysm which became gigantic and began to oppress a brain around it. However, subarachnoid hemorrhage often results in a so-called sudden death which causes death before a patient is admitted in a hospital and treated or a serious case and almost 50% of them have a bad outcome even in a current time of advanced medical techniques. Thus, early detection of unruptured cerebral aneurysm is an extremely important problem.

A cerebral aneurysm is detected in an early stage on the basis of three-dimensional images based on volume data including cerebral blood vessels obtained in an initial examination, but it may be diagnosed to have a small risk of rupture in some cases since a size of the cerebral aneurysm is small or the like. In that case, regular follow-up examinations are conducted by using CTA (computed tomography angiography), MRA (magnetic resonance angiography) and the like after the initial examination.

A medical image processing apparatus detects a cerebral aneurysm on the basis of volume data (three-dimensional data set) obtained in the initial examination and the follow-up examinations, makes measurements in accordance with measurement items (a neck area, a volume and the like of the cerebral aneurysm) of the cerebral aneurysm and displays its measurement result. A checker can observe a temporal change of the cerebral aneurysm on the basis of the display. In this case, an operator specifies positional parameters (spatial positions of an identification point of the cerebral aneurysm and a neck surface) for obtaining the measurement result by manually or semiautomatically (click operation) on the three-dimensional image based on the volume data including a cerebral blood vessel.

A detection supporting device and a detection method for detecting a candidate of a cerebral aneurysm from the volume data are disclosed.

According to a prior-art technique, in order to obtain a measurement result relating to a cerebral aneurysm at each follow-up examination, the operator needs to specify the positional parameters again manually or semiautomatically (click operation) on the three-dimensional image based on the volume data including the cerebral blood vessel at each follow-up examination. This specification operation is a burden on the operator, and there is a problem that variation is caused depending on a skill of the operator.

Thus, such a method can be considered for acquiring a measurement result in the follow-up examination by using the positional parameters specified in the initial examination by performing alignment of the volume data obtained in the follow-up examination with the volume data obtained in the initial examination. However, since a shape of the cerebral aneurysm changes by a growth thereof over time, simple alignment of the volume data cannot achieve appropriate alignment.

BRIEF DESCRIPTION OF THE DRAWINGS

In accompanying drawings.

DETAILED DESCRIPTION

A medical image processing apparatus and a medical image processing method according to this embodiment will be described by referring to the attached drawings.

To solve the above-described problems, the present embodiment provides the medical image processing apparatus including a processing circuitry configured to: set a first region and a second region different from the first region on first volume data and sets the first and second regions on second volume data, the first regions each including an observation target; perform a former alignment on the second regions of the first and second volume data; perform a latter alignment on the first regions of the first and second volume data by using a result of the former alignment; and apply a measurement condition used for a measurement of the observation target in the first volume data to a measurement of the observation target in the second volume data by using a result of the latter alignment.

To solve the above-described problems, the present embodiment provides the medical image processing method comprising steps of: obtaining first and second volume data from a storage; setting a first region and a second region different from the first region on the first volume data and setting the first and second regions on the second volume data, the first regions each including an observation target; performing a former alignment on the second regions of the first and second volume data; performing a latter alignment on the first regions of the first and second volume data by using a result of the former alignment; applying a measurement condition used for a measurement of the observation target in the first volume data to a measurement of the observation target in the second volume data by using a result of the latter alignment; and displaying a result of the measurement on a display.

1. First Embodiment

Figure 1:
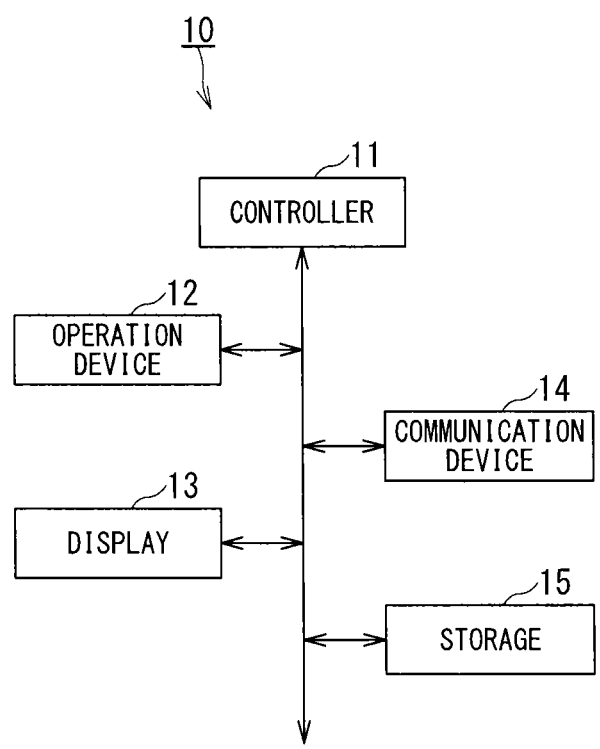
FIG. 1 is an outline diagram showing a hardware configuration of a medical image processing apparatus according to a first embodiment.

FIG. 1 is an outline diagram showing a hardware configuration of the medical image processing apparatus according to the first embodiment.

FIG. 1 shows a medical image processing apparatus 10 according to the first embodiment. The medical image processing apparatus 10 may be provided in a medical image system to which various devices are connected via a network, such as a medical image generating apparatus (medical image diagnosing apparatus) for generating a medical image, a server for storing/managing the medical image, an image reading terminal for obtaining a medical image stored in the server and displaying it on displaying unit for image-reading by a doctor, and the like. In the first embodiment, an example in which a single body of the medical image processing apparatus 10 realizes the present invention will be described, but functions in the medial image processing device 10 may be distributed in each constituting device of the medical image system so that the entire medical image system realizes the present invention.

The medical image processing apparatus 10 includes a controller 11, an operation device 12, a display 13, a communication device 14, and a storage 15.

The controller 11 is constituted by including a processing circuitry, a RAM (random access memory) and the like. The controller 11 reads out various control programs stored in the storage 15 for performing various calculations and integrally controls processing operations in each of the units 12 to 15.

The processing circuitry means any of dedicated and general-purpose CPUs (central processing units), an application specific integrated circuit (ASIC), and a programmable logic device. The programmable logic device may be, for example, any of a simple programmable logic device (SPLD), a complex programmable logic device (CPLD), and a field programmable gate array (FPGA). The processing circuitry achieves the functions 111-122 shown in FIG. 2 by reading and executing programs stored in a memory (or the storage 15) or directly implemented in the processing circuitry.

Furthermore, the processing circuitry may be configured by a single-piece circuitry, or an integrated circuitry including multiple independent circuitries. In the latter situation, memories for recording programs may be separately provided for the respective circuitries. Alternatively, one memory may store programs corresponding to the respective functions of circuitries.

The operation device 12 includes a keyboard, a mouse and the like. When the operation device 12 is operated by an operator, the operation device 12 generates an operation signal according to the operation and outputs it to the controller 11. The operation device 12 may include a touch panel integrally constituted with a display portion in the display 13.

The display 13 includes a display unit such as an LCD (liquid crystal display) or the like. The display 13 causes various types of display information, such as various operation screens, a three-dimensional image based on the volume data (three-dimensional data set) including information on a blood vessel, a measurement result of an observation target and the like, displayed on this display unit in accordance with an instruction from the controller 11. Here, the observation target includes an aneurysm such as a cerebral aneurysm, an aortic aneurysm (an aneurysm of a thoracic aorta and an abdominal aortic aneurysm), an internal organ aneurysm, a peripheral aneurysm, a coronary artery aneurysm and the like. Alternatively, the observation target includes a coarctation region by such as a plaque of a carotid artery, a plaque or a calcification of a coronary artery and the like.

Here, the three-dimensional image refers to an MPR (multi-planar reconstruction) image of an arbitrary section and a rendering (volume rendering, surface rendering) image of an arbitrary viewpoint based on first volume data.

The communication device 14 is constituted by a connector complying with a parallel connection specification or a serial connection specification. The communication device 14 performs transmission/reception of information with external devices on a network. The communication device 14 performs a communication operation with the external devices by receiving volume data obtained by an examination (three-dimensional imaging) by the medical image generating apparatus (not shown) from the medical image generating apparatus, a server (not shown) or the like and by transmitting a measurement result of an aneurysm in the medical image processing apparatus 10 to a reading terminal (not shown).

The storage 15 stores control programs used in the controller 11, various processing programs for a measurement of an aneurysm and the like and moreover, a positional parameter required for execution of each of the programs and data such as a measurement result. Moreover, the storage 15 stores the volume data received from the medical image generating apparatus, the server (not shown) and the like through the communication device 14. Here, third volume data is obtained by an examination by the medical image generating apparatus such as an X-ray diagnosing apparatus, an X-ray CT apparatus, an MRI apparatus, or an ultrasonic diagnosing apparatus similarly to the first volume data.

Figure 2:
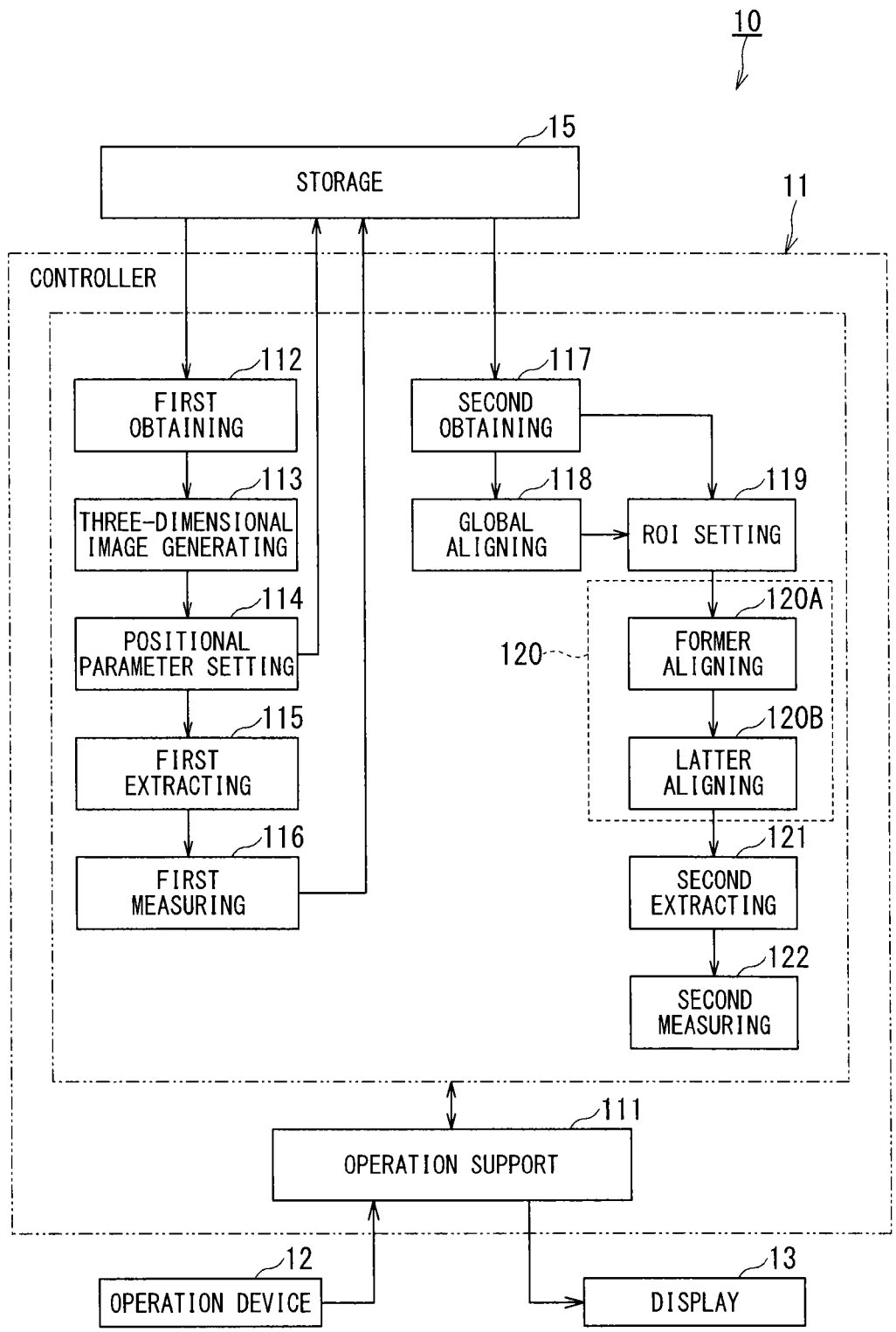
FIG. 2 is a block diagram showing a function of the medical image processing apparatus according to the first embodiment.

FIG. 2 is a block diagram showing a function of the medical image processing apparatus 10 according to the first embodiment.

When the processing circuitry of the controller 11 executes the program, the medical image processing apparatus 10 aligns a plurality of pieces of the volume data including blood vessel information and measures an observation target. The medical image processing apparatus 10 functions as an operation support 111, a first obtaining (reading-out) 112, a three-dimensional image generating 113, a positional parameter setting 114, a first extracting 115, a first measuring 116, a second obtaining (reading-out) 117, a global aligning 118, a ROI (region of interest) setting 119, a local aligning 120, a second extracting 121, and a second measuring 122.

In the first embodiment, a case in which a cerebral aneurysm is measured as an observation target will be described below.

The portions 111 to 122 of the medical image processing apparatus 10 will be described using a case in which they function in a software manner as an example, but a part of or the whole of the portions 111 to 122 may be provided on the medical image processing apparatus 10 in a hardware manner, respectively.

The operation support 111 is a user interface which can perform most of basic operations by the operation device 12 by frequently using graphics for display of the information to the operator on the display 13.

The first obtaining 112 obtains the volume data obtained by the examination of an object and to which the positional parameter and the measurement result are not associated from the storage 15. The volume data obtained by the first obtaining 112 includes information on the brain blood vessel. Here, the volume data is obtained by the examinations by the medical image generating apparatus such as the X-ray diagnosing apparatus, the X-ray CT apparatus, the MRI apparatus, or the ultrasonic diagnosing apparatus.

The three-dimensional image generating 113 generates a three-dimensional image on the basis of the volume data obtained by the first obtaining 112.

The positional parameter setting 114 sets the positional parameter for obtaining the measurement result relating to the cerebral aneurysm on the basis of the volume data obtained by the first obtaining 112 and the three-dimensional image generated by the three-dimensional image generating 113, the positional parameter being one of a measurement condition. The positional parameters include a spatial position (spatial coordinate) of an identification point relating to the cerebral aneurysm included in the volume data, a spatial position (spatial coordinate) of a boundary surface relating to the cerebral aneurysm and the like. When the observation target is the cerebral aneurysm, the boundary surface is a neck surface relating to the cerebral aneurysm. When the observation target is the cerebral aneurysm, the identification point relating to the cerebral aneurysm is used for extracting the cerebral aneurysm as shown hereinafter and the identification point is used as a center of an ROI as shown hereinafter.

For example, the positional parameter setting 114 sets the positional parameter on the basis of an instruction from the operation device 12 through the operation support 111 on the three-dimensional image displayed on the display 13 through the operation support 111. A spatial position of a neck surface as the positional parameter may be automatically determined on the basis of the spatial position of an identification point as the positional parameter.

The positional parameter set by the positional parameter setting 114 is displayed on the display 13 through the operation support 111. Moreover, the positional parameter is associated with the volume data and stored in the storage 15.

Figure 3:
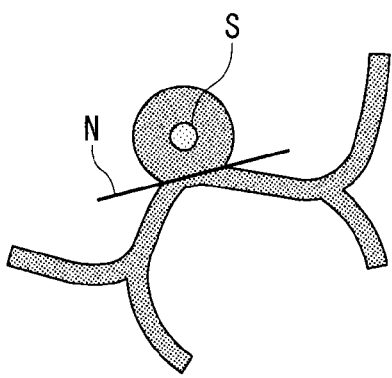
FIG. 3 is a diagram for explaining a setting method of positional parameters relating to a cerebral aneurysm.

FIG. 3 is a diagram for explaining a setting method of positional parameters relating to a cerebral aneurysm.

As shown in FIG. 3, an identification point S of the cerebral aneurysm is manually specified on the three-dimensional image generated by the three-dimensional image generating 113 (shown in FIG. 2), and a neck surface N of the cerebral aneurysm is manually specified or automatically determined. In this way, the identification point S and the spatial position of the neck surface N as the positional parameter are set.

Returning to the description of FIG. 2, the first extracting 115 extracts a region of the cerebral aneurysm including the spatial position of the identification point in the positional parameter set by the positional parameter setting 114 in compliance with the prior-art technique on the basis of the volume data obtained by the first obtaining 112.

The first measuring 116 obtains a measurement result by making measurement for the measurement items of the cerebral aneurysm on the basis of the region of the cerebral aneurysm extracted by the first extracting 115 and the spatial positions of the identification point and the neck surface as the positional parameter set by the positional parameter setting 114. The measurement items include the neck area of the cerebral aneurysm (an area of a surface where the cerebral aneurysm and the neck surface of the cerebral aneurysm cross each other), a volume of the cerebral aneurysm (a volume of the cerebral aneurysm separated by the neck surface) and the like.

The measurement result of the cerebral aneurysm obtained by the first measuring 116 may be displayed on the display 13 through the operation support 111. Alternatively, the measurement result of the cerebral aneurysm may be associated with the volume data and stored in the storage 15.

The second obtaining 117 obtains m-th volume data obtained in an examination of an m-th (m=1, 2, . . . , M) time phase and with which the positional parameter by the positional parameter setting 114 is associated and n-th volume data obtained in an examination of an n-th (n=2, . . . , N, n>m) time phase and with which the positional parameter is not associated from the storage 15. That is, the m-th volume data and the n-th volume data are accompanied by a temporal change. The volume data obtained by the second obtaining 117 include information on the brain blood vessel relating to the same object. Hereinafter, a case in which the m-th volume data is first volume data according to the examination in a first time phase (initial examination), and the n-th volume data is second volume data according to a follow-up examination (an examination in a second time phase subsequent to the initial examination) will be described as an example.

The global aligning 118 performs global alignment (linear conversion) of the second volume data to the first volume data obtained by the second obtaining 117. For example, the global aligning 118 can use a prior-art technique in which alignment processing is executed by using a marker or a prior-art technique in which an anatomical target point (a bone or the like) is determined in advance in a display target object and the alignment processing is executed by specifying a position thereof. If the first volume data and the second volume data subjected to global alignment in advance are stored in the storage 15, the global aligning 118 is not needed in the medical image processing apparatus 10.

Figure 4:
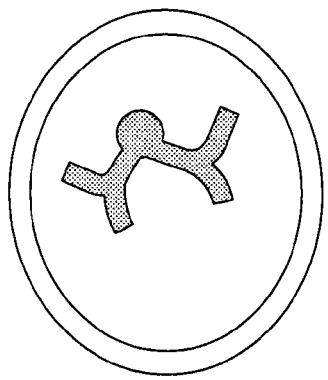
FIG. 4 is a diagram showing first volume data and second volume data after a global alignment.
Figure 4:
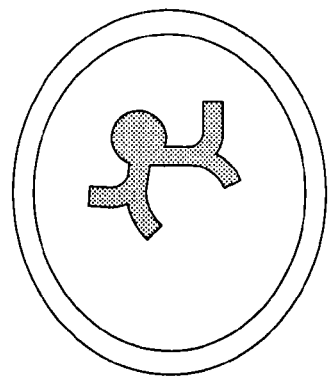

FIG. 4 is a diagram showing the first volume data and the second volume data after the global alignment.

Returning to the description of FIG. 2, the ROI setting 119 inputs the first volume data and the second volume data after the global alignment from the second obtaining 117 or the global aligning 118.

Then, the ROI setting 119 applies the spatial position of the identification point in the positional parameters associated with the first volume data to the second volume data. The ROI setting 119 sets a small ROI around the spatial position of the applied identification point and including the cerebral aneurysm to the second volume data. The ROI setting 119 sets the small ROI having a same size as the small ROI set in the second volume data around the spatial position of the associated identification point to the first volume data. For example, the small ROIs set to the first volume data and the second volume data, respectively, are balls having a same diameter and a same center.

Moreover, the ROI setting 119 sets a large ROI around the spatial position of the applied identification point and including the small ROI to the second volume data. The ROI setting 119 sets the large ROI having a same size as the large ROI around the spatial position of the associated identification point and set in the second volume data to the first volume data. For example, the large ROIs set to the first volume data and the second volume data, respectively, are balls having a same diameter and a same center.

Figure 5:
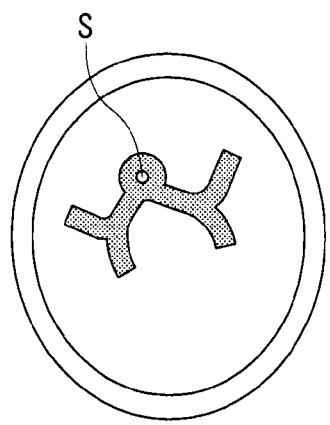
FIG. 5 is a diagram showing an identification point of the first volume data and an identification point of the second volume data.
Figure 5:
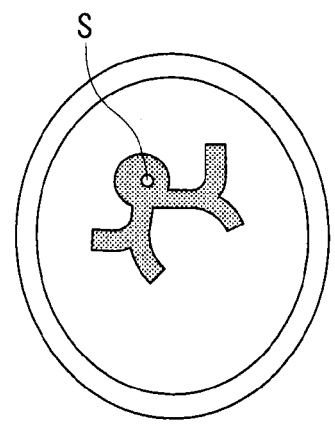
Figure 6:
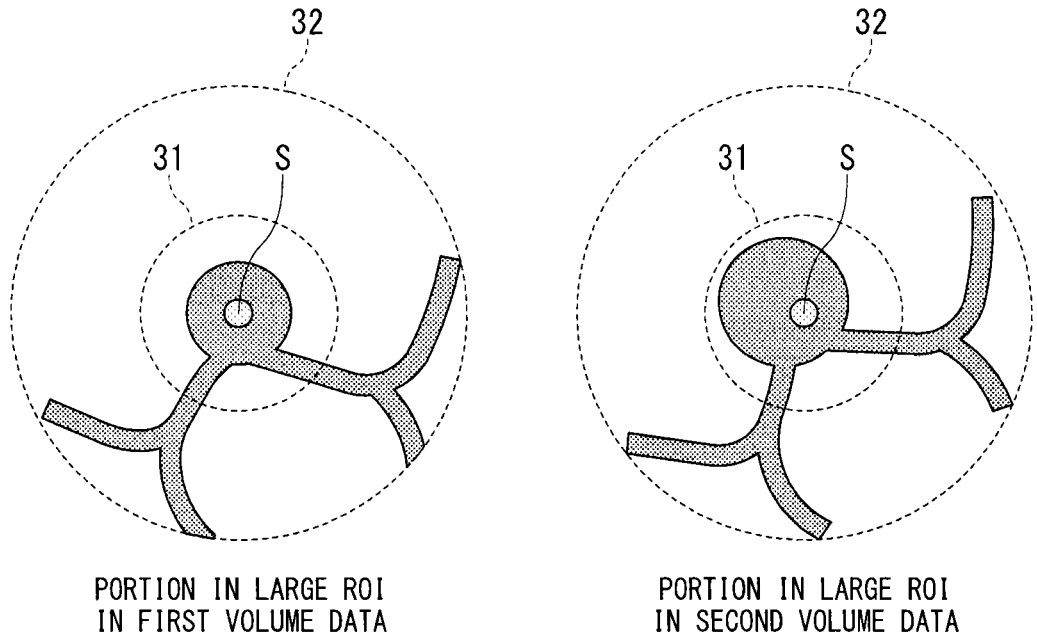
FIG. 6 is a diagram showing a portion in a large ROI in the first volume data and a portion in a large ROI in the second volume data.

FIGS. 5 and 6 are diagrams for explaining a ROI setting method. FIG. 5 is a diagram showing an identification point of the first volume data and an identification point of the second volume data. FIG. 6 is a diagram showing a portion in the large ROI in the first volume data and a portion in the large ROI in the second volume data.

A spatial position of the identification point S as a positional parameter associated with the first volume data shown on a left side in FIG. 5 is applied also to the second volume data shown on a right side in FIG. 5. Then, a small ROI 31 having a substantially ball shape around the spatial position of the identification point S and including the cerebral aneurysm of the second volume data is set to the first volume data and the second volume data shown in FIG. 5, respectively (shown in FIG. 6). Moreover, a large ROI 32 having a substantially ball shape around the spatial position of the identification point S and including the small ROI 31 is set to the first volume data and the second volume data, respectively (shown in FIG. 6).

Returning to the description of FIG. 2, the local aligning 120 includes a former aligning 120A and a latter aligning 120B.

The former aligning 120A performs a former alignment (a first alignment) on second regions of the first volume data and the second volume data. The second region of the second volume data is a peripheral region (a portion in the large ROI outside the small ROI) not including the cerebral aneurysm in the second volume data. The second region of the first volume data is a peripheral region (a portion in the large ROI outside the small ROI) at a same position as the peripheral region in the first volume data. For example, the former aligning 120A performs a local alignment (linear conversion) of the peripheral region of the second volume data to the peripheral region of the first volume data.

Specifically, the former aligning 120A subjects a portion in the large ROI having a voxel value of the portion in the small ROI converted to "0" in the second volume data to local alignment with respect to a portion in the large ROI having the voxel value of the portion in the small ROI converted to "0" in the first volume data.

Figure 7:
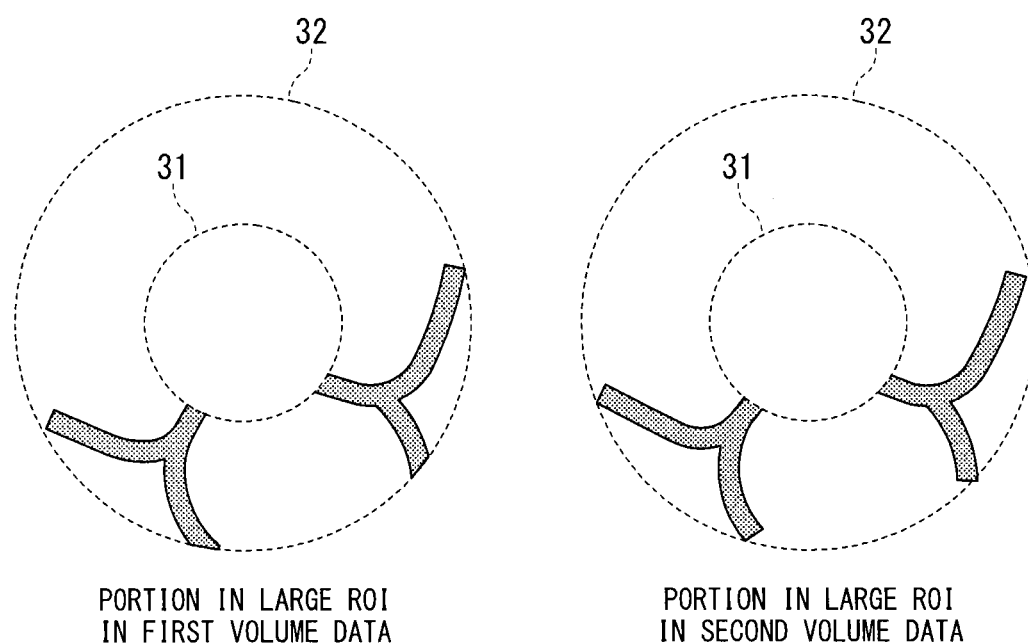
FIG. 7 is a diagram showing the portion in the large ROI in the first volume data and the portion in the large ROI after a local alignment in the second volume data.

FIG. 7 is a diagram showing the portion in the large ROI in the first volume data and the portion in the large ROI after local alignment in the second volume data.

The large ROI 32 with a voxel value in the small ROI 31 converted to "0" in the first volume data is set, and the large ROI 32 having the voxel value in the small ROI 31 converted to "0" in the second volume data is set. Then, as shown in FIG. 7, the portion in the large ROI 32 in the second volume data is subjected to local alignment with respect to the portion in the large ROI 32 in the first volume data.

Figure 8:
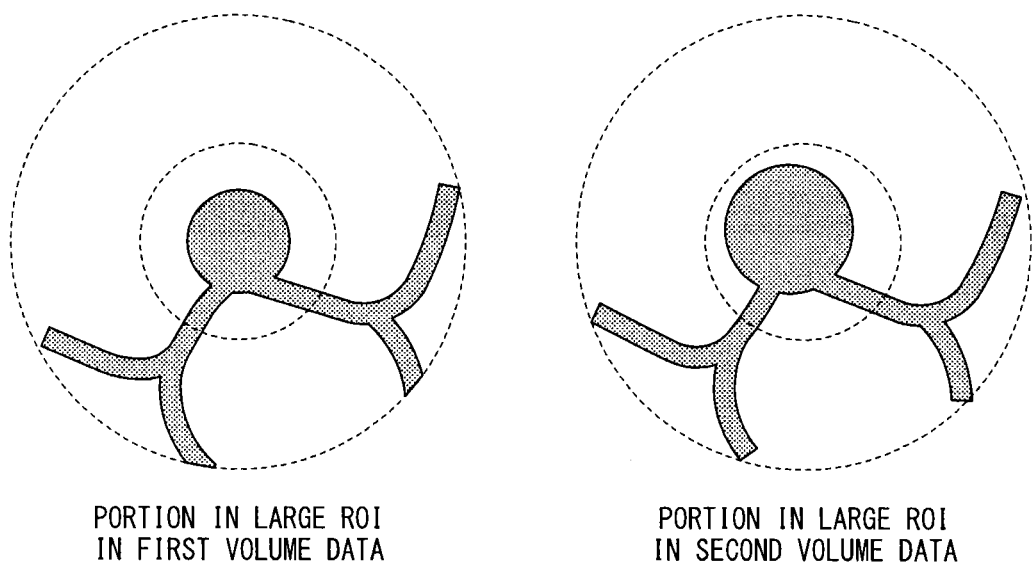
FIG. 8 is a diagram showing the portion in the large ROI in the first volume data, the portion in the large ROI after a former alignment in the second volume data, and the portion in the small ROI after a latter alignment in the second volume data.

Returning to the description of FIG. 2, the latter aligning 120B performs a latter alignment (a second alignment) on first regions of the first volume data and the second volume data by using a result of the former alignment. The first region of the first volume data is the small ROI in the first volume data. The first region of the second volume data is the small ROI in the second volume data. For example, the latter aligning 120B performs an alignment to move the portion in the small ROI in the second volume data in accordance with the moving amount by the former aligning 120A. FIG. 8 is a diagram showing the portion in the large ROI in the first volume data, the portion in the large ROI after the former alignment in the second volume data, and the portion in the small ROI after the latter alignment in the second volume data.

Returning to the description of FIG. 2, the second extracting 121 extracts a region of the cerebral aneurysm from the portion in the small ROI of the second volume data after the alignment by the latter aligning 120B, in accordance with the prior-art technique.

The second measuring 122 applies the spatial positions of the identification point and the neck surface as the positional parameters associated with the first volume data to the region of the cerebral aneurysm extracted by the second extracting 121. Then, the second measuring 122 performs measurement for the measurement items of the cerebral aneurysm and obtains a measurement result on the basis of the region of the cerebral aneurysm extracted by the second extracting 121 and the spatial positions of the applied identification point and neck surface. The measurement result on the cerebral aneurysm obtained by the second measuring 122 is displayed on the display 13 through the operation support 111 or stored in the storage 15.

Figure 9:
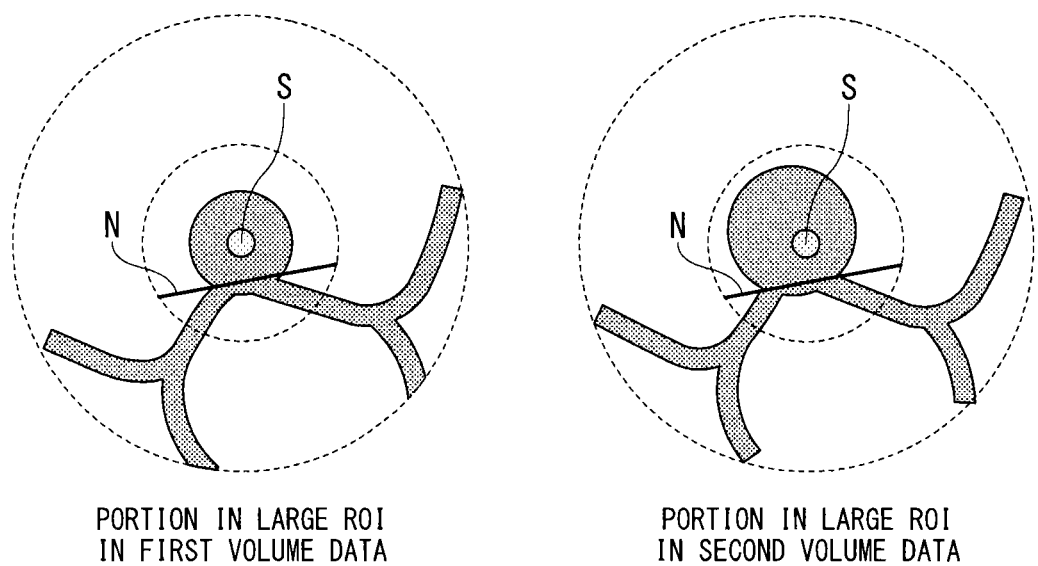
FIG. 9 is a diagram for explaining a measuring method relating to the cerebral aneurysm based on the second volume data.

FIG. 9 is a diagram for explaining a measuring method relating to the cerebral aneurysm based on the second volume data.

On a left side in FIG. 9, the portion in the large ROI in the first volume data and the spatial positions of the identification point S and the neck surface N as the positional parameters associated with the first volume data are shown, respectively. On a right side in FIG. 9, the portion in the large ROI after a peripheral region in the second volume data has been aligned in the former alignment and a center region has been aligned in the latter alignment, and the spatial positions of the identification point S and the neck surface N as the applied positional parameters are shown, respectively.

Since the second volume data is locally aligned, the portion in the small ROI in the second volume data is arranged at a proper position with respect to the portion in the small ROI in the first volume data as shown in FIG. 9. Thus, the measurement result based on the positional parameter applied to the second volume data is also accurate and precise.

Returning to the description of FIG. 2, the operation support 111 causes the measurement result by the second measuring 122 to be displayed on the display 13. For example, the operation support 111 causes a three-dimensional image based on the portion in the large ROI (or the small ROI) in the first volume data shown in FIG. 9 and a three-dimensional image based on the portion in the large ROI (or the small ROI) in the second volume data to be displayed on the display 13.

Figure 10:
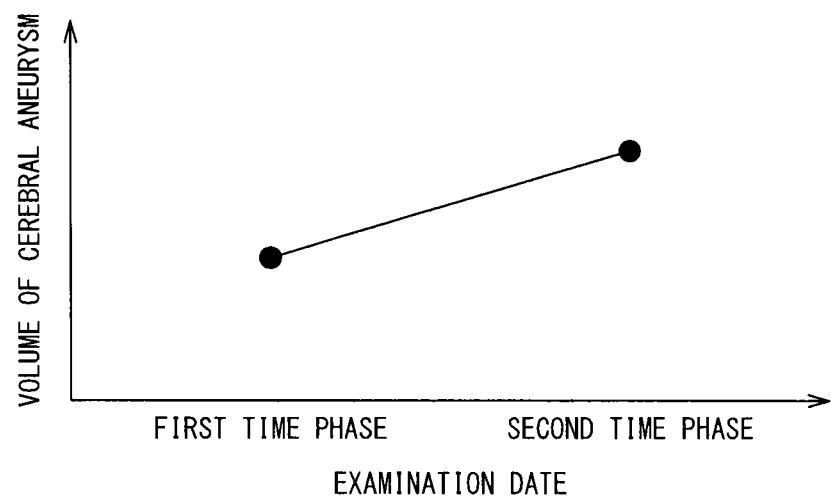
FIG. 10 is a diagram showing a display example of a measurement result relating to the cerebral aneurysm based on the second volume data.

FIG. 10 is a diagram showing a display example of the measurement result relating to the cerebral aneurysm based on the second volume data.

FIG. 10 shows a measurement result in a case in which not only the positional parameter based on the first volume data but also the measurement result is associated with the first volume data as a graph. The graph shown in FIG. 10 shows a measurement result relating to a volume of the cerebral aneurysm associated with the first volume data at a first time phase. Moreover, the graph shown in FIG. 10 shows a measurement result relating to a region of the cerebral aneurysm extracted by the second extracting 121 (shown in FIG. 2) and a volume of the cerebral aneurysm based on the applied positional parameter at a second time phase.

As described above, according to the portions 117 to 122, the medical image processing apparatus 10 can acquire the measurement result relating to the second volume data accurately and precisely by using the positional parameter set by using the first volume data even if the positional parameter is not determined manually or semiautomatically for the second volume data.

The global aligning 118 is described for the case in which the spatial position of the second volume data is converted to the spatial position of the first volume data for the global alignment. However, the case is not limiting. It is only necessary that the global aligning 118 subjects the spatial position of the first volume data and the spatial position of the second volume data to global alignment.

For example, the global aligning 118 may convert the spatial position of the first volume data to the spatial position of the second volume data or may convert the spatial position of the first volume data and the spatial position of the second volume data to a spatial position which becomes a reference. In those cases, the positional parameter associated with the first volume data is also converted in accordance with conversion of the first volume data.

Subsequently, an operation of the medical image processing apparatus 10 according to the first embodiment will be described by using FIGS. 1, 11, and 12.

Figure 11:
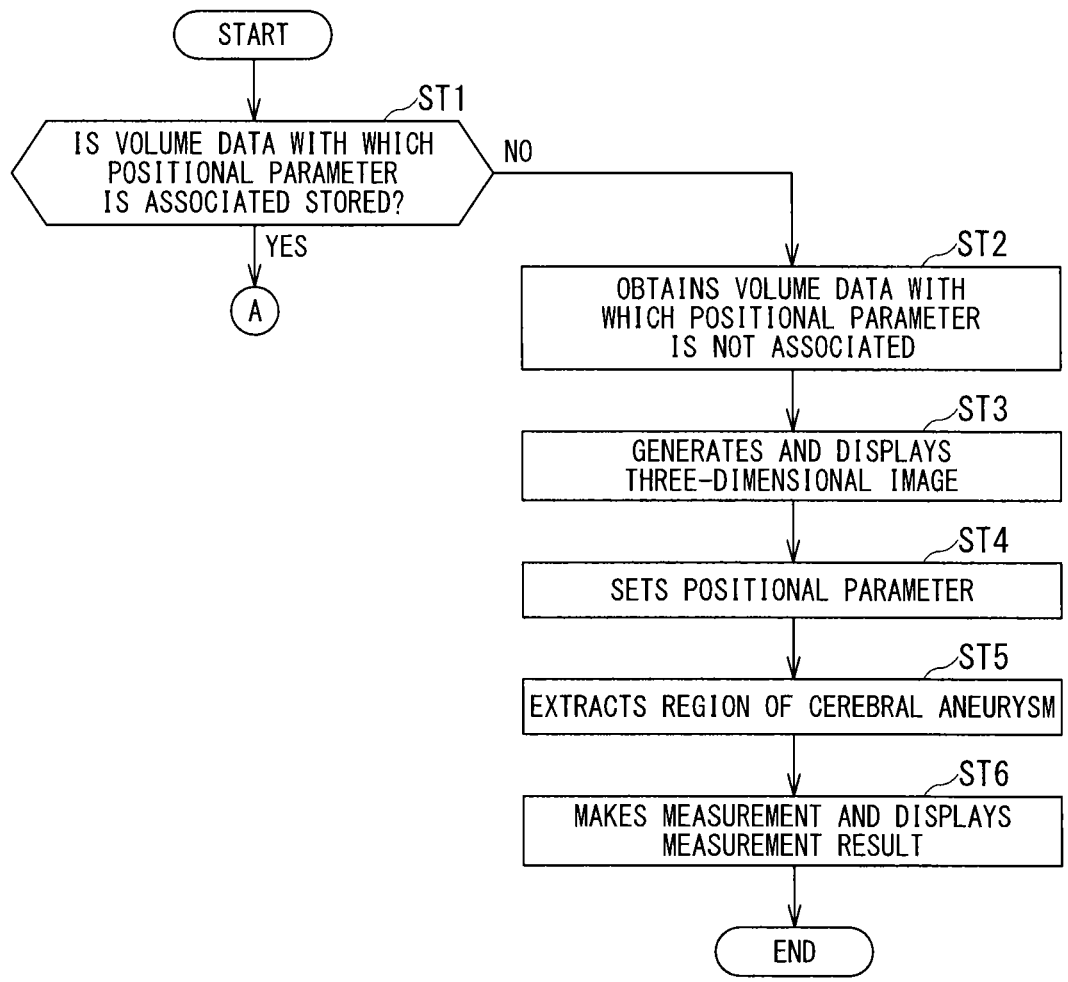
FIG. 11 is a former part of a flowchart showing an operation of the medical image processing apparatus according to the first embodiment.
Figure 12:
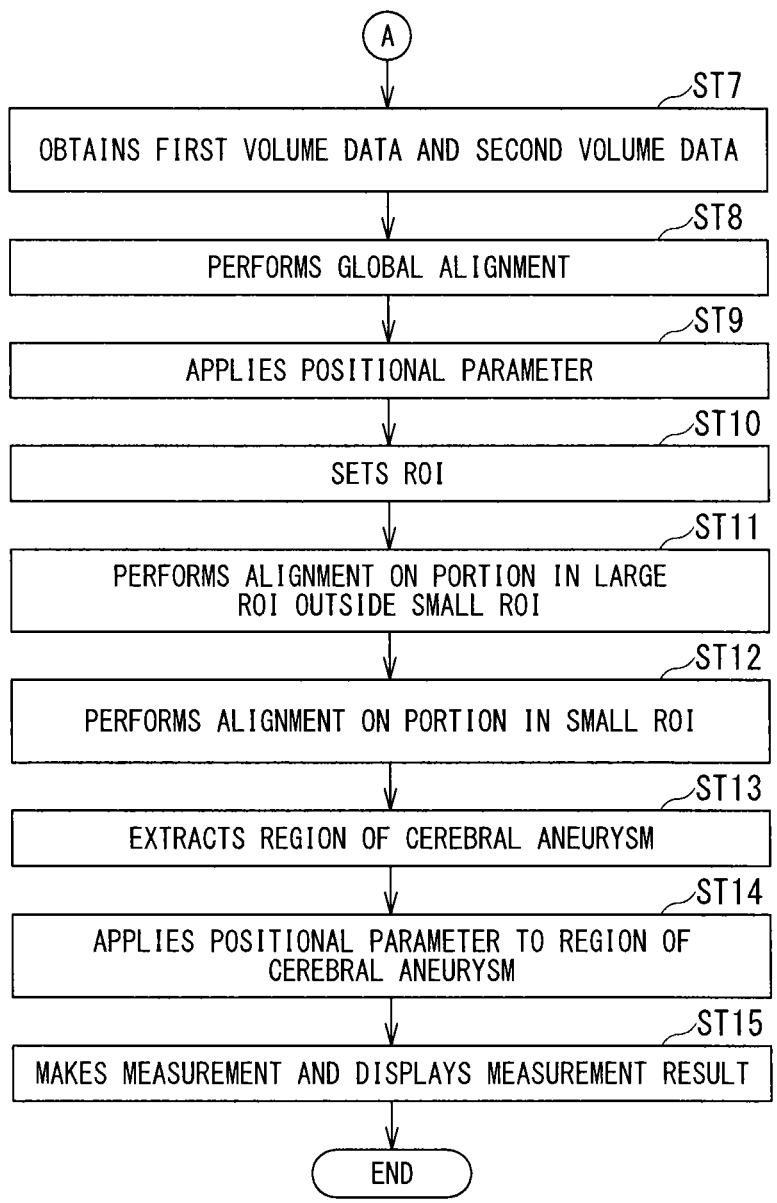
FIG. 12 is a latter part of the flowchart showing the operation of the medical image processing apparatus according to the first embodiment.

FIGS. 11 and 12 are flowcharts showing an operation of the medical image processing apparatus 10 according to the first embodiment.

FIG. 11 is an operation for setting the positional parameter through a manual/semiautomatic operation on the basis of the volume data and for associating the positional parameter with the volume data. For example, FIG. 11 is an operation for the volume data according to the initial examination to be associated with the positional parameter based on the volume data.

On the other hand, FIG. 12 is an operation for automatically setting the positional parameter according to the n-th volume data on the basis of the m-th volume data with association and the n-th volume data without association. For example, FIG. 12 is an operation for automatically setting the positional parameter according to the second volume data on the basis of the first volume data according to the initial examination, the positional parameter associated with that, and the second volume data according to the follow-up examination.

Explaining FIG. 11, the medical image processing apparatus 10 determines whether or not volume data with which a positional parameter is associated is stored, the volume data being included in volume data stored in the storage 15 (Step ST1). If determination at Step ST1 is YES, that is, if the medical image processing apparatus 10 determines that the volume data with which the positional parameter is associated is stored in the storage 15, a routine proceeds to an operation at Step ST7 shown in FIG. 12.

On the other hand, if the determination at Step ST1 is NO, that is, if the medical image processing apparatus 10 determines that the volume data with which the positional parameter is associated is not stored in the storage 15, the medical image processing apparatus 10 obtains volume data without association from the storage 15 (Step ST2).

The medical image processing apparatus 10 generates a three-dimensional image on the basis of the volume data obtained at Step ST2 and displays it on the display 13 (Step ST3).

The medical image processing apparatus 10 sets the positional parameter for obtaining a measurement result relating to the cerebral aneurysm on the basis of the volume data obtained at Step ST2 and the three-dimensional image generated at Step ST3 (Step ST4).

The medical image processing apparatus 10 extracts a region of the cerebral aneurysm including the spatial position of the identification point in the positional parameters set at Step ST4 on the basis of the volume data obtained at Step ST2 (Step ST5).

The medical image processing apparatus 10 makes measurement for the measurement items of the cerebral aneurysm and displays the measurement result on the display 13 on the basis of the region of the cerebral aneurysm extracted at Step ST5 and the spatial positions of the identification point and the neck surface as the positional parameters set at Step ST4 (Step ST6).

If the determination at Step ST1 is YES, moving to the description of FIG. 12, the medical image processing apparatus 10 obtains the volume data with which the positional parameter is associated (the first volume data according to the first time phase) and the volume data with which the positional parameter is not associated (second volume data according to the second time phase) from the storage 15 (Step ST7).

The medical image processing apparatus 10 subjects the first volume data and the second volume data obtained at Step ST7 to the global alignment (Step ST8).

The medical image processing apparatus 10 applies the spatial position of the identification point in the positional parameters associated with the first volume data to the second volume data (Step ST9).

The medical image processing apparatus 10 sets a small ROI around the spatial position of the identification point applied at Step ST9 and including the cerebral aneurysm to the second volume data (Step ST10). The medical image processing apparatus 10 sets a small ROI having a same size as the small ROI around the spatial position of the associated identification point and set in the second volume data to the first volume data (Step ST10). Moreover, the medical image processing apparatus 10 sets a large ROI around the spatial position of the identification point applied at Step ST9 and including the small ROI to the second volume data (Step ST10). The medical image processing apparatus 10 sets a large ROI having the same size as the large ROI around the spatial position of the associated identification point and set in the second volume data to the first volume data (Step ST10).

The medical image processing apparatus 10 subjects the portion (the second region) in the large ROI outside the small ROI in the second volume data to the alignment with respect to the portion in the large ROI outside the small ROI in the first volume data and thereby performs the alignment (Step ST11).

The medical image processing apparatus 10 moves the portion (the first region) in the small ROI in the second volume data in accordance with the moving amount of the alignment at Step ST11 and thereby performs the alignment (Step ST12).

The medical image processing apparatus 10 extracts a region of the cerebral aneurysm on the basis of the portion in the small ROI after movement at Step ST12 (Step ST13).

The medical image processing apparatus 10 applies the spatial positions of the identification point and the neck surface as the positional parameters associated with the first volume data to the region of the cerebral aneurysm extracted at Step ST13 (Step ST14).

The medical image processing apparatus 10 makes measurement for the measurement items of the cerebral aneurysm on the basis of the region of the cerebral aneurysm extracted at Step ST13 and the spatial positions of the identification point and the neck surface as the positional parameters applied at Step ST14 and displays the measurement result on the display 13 (Step ST15).

According to the medical image processing apparatus 10 and the medical image processing method according to the first embodiment, the measurement condition used for the measurement of the cerebral aneurysm of the first volume data is applied to the measurement of the cerebral aneurysm of the second volume data. Then the measurement is performed on the measurement items of the cerebral aneurysm on the basis of the spatial positions of the identification point and the neck surface, and the measurement result is obtained. The measurement items include the neck area of the cerebral aneurysm (an area of a surface where the cerebral aneurysm and the neck surface cross each other), the volume of the cerebral aneurysm (a volume of the cerebral aneurysm separated by the neck surface) and the like.

According to the medical image processing apparatus 10 and the medical image processing method according to the first embodiment, the m-th volume data and the n-th volume data including the information on the blood vessel can be appropriately aligned. Moreover, according to the medical image processing apparatus 10 and the medical image processing method according to the first embodiment, since the m-th volume data and the n-th volume data including the information on the blood vessel can be appropriately aligned, a labor for specifying the positional parameter manually or semiautomatically on the three-dimensional image based on the n-th volume data at each examination (follow-up examination) at the n-th time phase can be saved, a burden on the operator is reduced, and dependence on the skill of the operator is not necessary.

2. Second Embodiment

In the medical image processing apparatus 10 and the medical image processing method according to the first embodiment, a cerebral aneurysm as the observation target is described as an example, but the observation target is not limited to that case. For example, the observation target may be an aortic aneurysm (an aneurysm of the thoracic aorta and an abdominal aortic aneurysm), for example. In the second embodiment, a case in which the observation target is an aortic aneurysm will be described.

A hardware configuration of the medical image processing apparatus 10 according to the second embodiment is equal to that shown in FIG. 1. A function of the medical image processing apparatus 10 according to the second embodiment is equal to that shown in FIG. 2. An operation of the medical image processing apparatus 10 according to the second embodiment is equal to that shown in FIGS. 11 and 12. The volume data includes information on an aorta.

Figure 13:
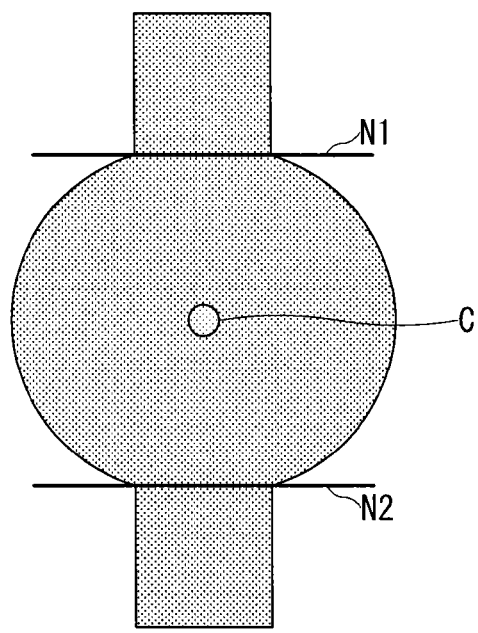
FIG. 13 is a diagram for explaining a method of setting positional parameters relating to a true aortic aneurysm.

FIG. 13 is a diagram for explaining a method of setting a positional parameter relating to a true aortic aneurysm.

As shown in FIG. 13, on a three-dimensional image generated by the three-dimensional image generating 113 (shown in FIG. 2), a center point C of the true aortic aneurysm is manually and automatically specified, and the boundary surface relating to the true aortic aneurysm are manually specified or automatically determined. When the observation target is the true aortic aneurysm, the boundary surface is a pair of edge surfaces N1 and N2 of the true aortic aneurysm, the edge surfaces N1 and N2 being perpendicular to the aorta. As described above, spatial positions of the center point C, and the edge surfaces N1 and N2 as the positional parameters are set. The true aortic aneurysm refers to a symptom of large swelling while a blood vessel wall of an aorta is maintained. The center point C of the aortic aneurysm does not have to be used for extracting the aorta differently from the above-mentioned identification point, the center point C is used as a center of an after-mentioned ROI.

As is the case in true aortic aneurysm, in the case of a dissecting aortic aneurysm and a false aortic aneurysm, the boundary surface is a pair of edge surfaces, the edge surfaces being perpendicular to the aorta. The dissecting aortic aneurysm refers to a symptom in which a crack occurs in an intima, blood enters between the intima and a media, the two membranes are peeled off each other, the blood enters a peeled portion, and dissociation (tear) swells. The false aortic aneurysm refers to a symptom in which a part of a wall of an aorta is broken in three layers of an intima, a media, and an adventitia, and blood leaking from there compresses tissues around there and forms an aneurysm.

Figure 14:
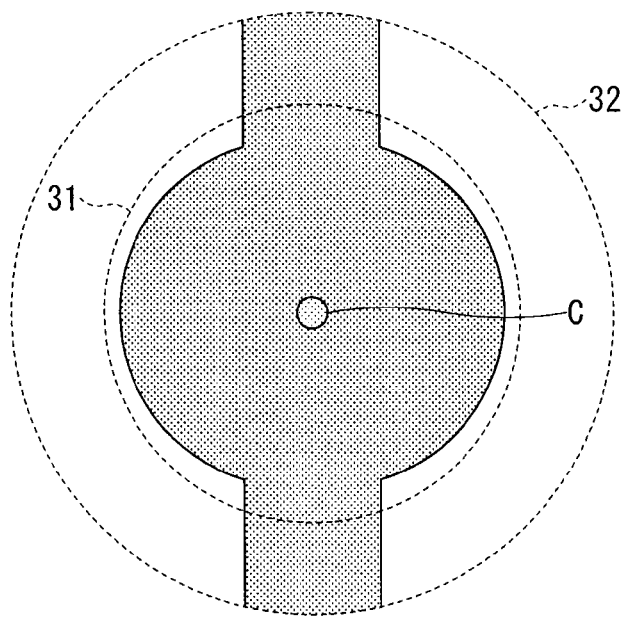
FIG. 14 is a diagram showing a portion in a large ROI in the first volume data.

FIG. 14 is a diagram showing a portion in a large ROI in the first volume data.

The small ROI 31 around the spatial position of the center point C and having a substantially ball shape including an aortic aneurysm of the second volume data is set to the first volume data. Moreover, the large ROI 32 around the spatial position of the center point C and having a substantially ball shape including the small ROI 31 is set to the first volume data.

As described by using FIG. 6, the small ROI 31 and the large ROI 32 are set also to the second volume data.

According to the medical image processing apparatus 10 and the medical image processing method according to the second embodiment, the measurement condition used for the measurement of the aortic aneurysm of the first volume data is applied to for the measurement of the aortic aneurysm of the second volume data. Then the measurement is performed on the measurement items of the aortic aneurysm on the basis of the spatial positions of the center point and the edge surfaces, and the measurement result is obtained. The measurement items include edge areas of the aortic aneurysm (areas of surfaces where the aortic aneurysm and each of the edge surfaces cross each other), a volume of the aortic aneurysm (a volume of the aortic aneurysm placed between the edge surfaces) and the like.

Alternatively, when the volume data includes information of the carotid artery, the observation target may be the coarctation region by the plaque of the carotid artery. Alternatively, when the volume data includes information of the coronary artery, the observation target may be the coarctation region by the plaque or the calcification of the coronary artery. In any of these cases, the spatial positions of the center point C and the edge surfaces N1 and N2 (shown in FIG. 13) defining a coarctation range are set. When the edge surfaces N1 and N2 are defined as the coarctation range, using the method in the case of the aorta, the measurement condition used for the measurement of the coarctation region of the first volume data is applied to the measurement of the coarctation region of the second volume data. Note that phases of heart rate of the first volume data and the second volume data are expected to be approximately-same when the observation target is the coarctation region by the plaque or the calcification of the coronary artery.

According to the medical image processing apparatus 10 and the medical image processing method according to the second embodiment, the m-th volume data and the n-th volume data including the information on the blood vessel can be appropriately aligned. Moreover, according to the medical image processing apparatus 10 and the medical image processing method according to the second embodiment, since the m-th volume data and the n-th volume data including the information on the blood vessel can be appropriately aligned, a labor for specifying the positional parameter manually or semiautomatically on the three-dimensional image based on the n-th volume data at each examination (follow-up examination) at the n-th time phase can be saved, a burden on the operator is reduced, and dependence on the skill of the operator is not necessary.

3. Variation

In the medical image processing apparatus 10 and the medical image processing method according to the first and second embodiments, the first volume data and the second volume data accompanied by temporal changes are described as an example, but the first volume data and the second volume data are not limited to that case. It is only necessary that the first volume data and the second volume data are different data relating to a same portion.

For example, the first volume data and the second volume data are different data relating to the same portion generated by a same type of the medical image generating apparatus under different imaging conditions. Moreover, the first volume data and the second volume data are different data relating to the same portion generated by different types of the medical image generating apparatuses, for example. Hereinafter, the latter case will be described.

The first volume data is generated by the X-ray CT apparatus which is a first medical image generating apparatus. Whether or not treatment is needed is determined by the operator in accordance with an image based on the first volume data. If it is determined that the treatment is needed, 3D imaging is performed by an X-ray diagnosing apparatus (angio apparatus) which is a second medical image generating apparatus during a treatment planning by the angio apparatus, whereby the second volume data is generated. Since an image based on the second volume data is used for the treatment planning, it has higher resolution in general than that of an image based on the first volume data.

A measurement condition used for measurement of an observation target set by the first volume data generated by the X-ray CT apparatus can be applied to measurement of the observation target in the second volume data generated by the angio apparatus.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus comprising a processing circuitry configured to:
    set a first region and a second region different from the first region on first volume data and sets the first and second regions on second volume data, the first regions each including an observation target;
    perform a former alignment on the second regions of the first and second volume data;
    perform a latter alignment on the first regions of the first and second volume data by using a result of the former alignment; and
    apply a measurement condition used for a measurement of the observation target in the first volume data to a measurement of the observation target in the second volume data by using a result of the latter alignment.

2. The medical image processing apparatus according to claim 1, wherein the processing circuitry is configured to:
    extract a region of an observation target included in the first region after the latter alignment in the second volume data; and
    apply a measurement condition associated with the first volume data to the region of the observation target, and perform the measurement of the observation target in the second volume data.

3. The medical image processing apparatus according to claim 1, wherein the processing circuitry is configured to:
    set a small region that is the first region including the observation target in the second volume data and a large region including the small region to the second volume data, respectively, and sets a small region and a large region at a same position as the small region and the large region to the first volume data, respectively; and
    set a portion in the large region outside the small region in the first volume data to the second region in the first volume data and a portion in the large region outside the small region in the second volume data to the sesond region in the second volume data.

4. The medical image processing apparatus according to claim 3, wherein
    the processing circuitry is configured to set the small region having a substantially ball shape having a center at a same position as an identification point of the observation target as the measurement condition associated with the first volume data and the large region having a substantially ball shape including the small region to the second volume data, respectively.

5. The medical image processing apparatus according to claim 1, wherein
    the processing circuitry is configured to perform a global alignment on raw data of the first and second volume data, and obtain the first and second volume data.

6. The medical image processing apparatus according to claim 1, wherein
the observation target is a cerebral aneurysm, the second regions include information on a brain blood vessel, and the measurement condition is a neck surface.

7. The medical image processing apparatus according to claim 6, wherein
the processing circuitry is configured to measure at least one of an area of a surface where the cerebral aneurysm and the neck surface cross each other, and of a volume of the cerebral aneurysm separated by the neck surface.

8. The medical image processing apparatus according to claim 6, wherein
the processing circuitry is configured to display a measurement result of the observation target in the second volume data on a display, the observation target being the cerebral aneurysm.

9. The medical image processing apparatus according to claim 8, wherein
the processing circuitry is configured to display a measurement result associated with the first volume data and the measurement result in the second volume data on the display.

10. The medical image processing apparatus according to claim 1, wherein
the observation target is an aortic aneurysm, the second regions include information on an aorta, and the measurement condition is a pair of edge surfaces of the aortic aneurysm, the edge surfaces being perpendicular to the aorta.

11. The medical image processing apparatus according to claim 10, wherein
the processing circuitry is configured to measure at least one of areas of surfaces where the aortic aneurysm and each of the edge surfaces cross each other, and of a volume of the aortic aneurysm placed between the edge surfaces.

12. The medical image processing apparatus according to claim 1, wherein
the first and second volume data are accompanied by temporal changes.

13. The medical image processing apparatus according to claim 1, wherein
the first and second volume data are generated by a same type of medical image generating apparatus under different imaging conditions.

14. The medical image processing apparatus according to claim 1, wherein
the first and second volume data are generated by different types of medical image generating apparatuses.

15. The medical image processing apparatus according to claim 14, wherein
an image based on the first volume data has a resolution lower than that of an image based the second volume data.

16. A medical image processing method comprising steps of:
obtaining first and second volume data from a storage;
setting a first region and a second region different from the first region on the first volume data and setting the first and second regions on the second volume data, the first regions each including an observation target;
performing a former alignment on the second regions of the first and second volume data;
performing a latter alignment on the first regions of the first and second volume data by using a result of the former alignment;
applying a measurement condition used for a measurement of the observation target in the first volume data to a measurement of the observation target in the second volume data by using a result of the latter alignment; and
displaying a result of the measurement on a display.

* * * * *